United States Patent
Wagner

[11] Patent Number: 6,083,235
[45] Date of Patent: Jul. 4, 2000

[54] BREATH SYSTEM APPLIANCE WITH DORSAL APPLICATOR AND SCRAPER

[75] Inventor: Eugene C. Wagner, Pacific Palisades, Calif.

[73] Assignee: Dental Concepts, LLC, Paramus, N.J.

[21] Appl. No.: 09/307,705

[22] Filed: May 10, 1999

[51] Int. Cl.[7] .................................................. A61B 17/00
[52] U.S. Cl. ........................................................... 606/161
[58] Field of Search ............................... 606/1, 160, 161; 600/56

[56] References Cited

U.S. PATENT DOCUMENTS

| | | |
|---|---|---|
| D. 243,422 | 2/1977 | Varga . |
| D. 309,528 | 7/1990 | Valenti . |
| 2,218,072 | 10/1940 | Runnels ................................. 606/161 |
| 2,491,274 | 12/1949 | McNeill ................................. 606/161 |
| 3,943,592 | 3/1976 | Bhaskar et al. . |
| 4,079,478 | 3/1978 | Andrews, Sr. . |
| 5,226,197 | 7/1993 | Nack et al. . |
| 5,638,810 | 6/1997 | Yavitz . |
| 5,735,864 | 4/1998 | Heisinger, Jr. . |
| 5,774,925 | 7/1998 | Pryor, III . |
| 5,779,654 | 7/1998 | Foley et al. . |

*Primary Examiner*—Michael Buiz
*Assistant Examiner*—William Lewis
*Attorney, Agent, or Firm*—Natter & Natter

[57] ABSTRACT

A breath system appliance includes a planar thin elongate body having an applicator head at one end and a scraper head at the other end. The applicator head includes a sponge impregnated with a dorsal conditioning medium. The medium may include an antibacterial agent, an antiseptic agent, a flavoring agent, an oxidizing agent and an anesthetizing agent. The conditioning medium is applied as a coating to dorsal surfaces of a user. The scraper head is thereafter applied against dorsal surfaces of the user to dislodge food debris and other odor generating matter from the dorsum of the user. The appliance may be carried in a liquid impervious sealed packet.

19 Claims, 3 Drawing Sheets

BREATH SYSTEM APPLIANCE WITH DORSAL APPLICATOR AND SCRAPER

BACKGROUND OF THE INVENTION

1. Field of the Invention

The present invention relates generally to oral hygiene appliances and more specifically to devices which promote oral hygiene by removing debris from one's tongue.

2. Antecedents of the Invention

The general public has been highly conscious of oral hygiene, not only from a social standpoint, but additionally in its relationship to overall health. While basic oral hygiene devices such as toothbrushes, toothpaste, tooth powder, interdental stimulators, interproximal brushes, dental floss, toothpicks and dental picks, e.g. U.S. Pat. No. 4,326,548, have been in use through the years, in recent years there has been a proliferation of do-it-yourself oral hygiene cosmetic products, including various tooth whitening preparations, e.g. U.S. Pat. No. 5,084,268 as well as tooth polishers, for improvement of the appearance of one's mouth.

The public has also been cognizant of the need to combat mouth malodor in daily social encounters. Various factors have been attributed to the generation of oral malodor including improper brushing, failure to brush and/or failure to floss. Other factors include the presence of various compounds in the oral cavity which are alleged to cause malodor, such as hydrogen sulfide.

It has also been recognized that minute food particles and debris as well as odor producing bacteria resided on the tongue, particularly on the dorsal (upper) surface thereof, i.e. the dorsum.

The dorsum has been characterized as a rough surface which is covered with papillae. The anterior of the dorsum is covered with fungiform papillae and the posterior (pharyngeal) surface is covered with fungiform papillae interspersed with filiform papillae.

Food particles and the breakdown products of foods became lodged in crevices between the papillae. Dense bacterial populations and the many bacterial species resident on the dorsum have been known to colonize. It is believed that the dorsum is the source of most of the bacteria in the oral cavity and the source of oral malodor.

The prevalent use of mouthwashes, breath mints and breath sprays did not alleviate or reduce the source of malodor, but merely served to mask the condition.

Various tongue scrapers such as those disclosed in the patents to Heisinger (U.S. Pat. No. 5,735,864), Andrews (U.S. Pat. No. 4,079,478), Nack (U.S. Pat. No. 5,226,179) and Bhaskar (U.S. Pat. No. 3,943,592) are among the devices which have been suggested for cleaning the tongue to remove food debris and other material accumulated on the dorsum.

Although such devices were capable of scraping the dorsum and loosening debris accumulated thereon, absent was the ability to adequately scrape the pharyngeal tissue surface due to the tendency of any scraping appliance to induce a gag reflex. Additionally, treatment of existing malodor conditions required the employment of a mouthwash or other breath freshener since tongue scrapers provided primarily prophylactic, rather than immediate relief.

Further, none of the prior devices gained a measure of consumer acceptance, either because they were too difficult to use, to costly to manufacture, or were otherwise unsuited for general use.

SUMMARY OF THE INVENTION

A breath system appliance with dorsal applicator and scraper includes a generally flat, relatively thin, elongate body. Projecting transversely from the longitudinal axis of the body at one end thereof is a generally planar, relatively thin applicator head while a scraper head projects transversely from the other end of the body. Adhered to a face of the applicator head is a thin sponge layer carrying a supply of a liquid based dorsal conditioning medium. The medium may include an antibacterial agent, antiseptic agent, flavoring agent, and an oxidizing agent. Typical constituents include zinc chloride, thymol, eucalyptus oil, menthol, peroxides and stabilized chlorine dioxide. The conditioning medium is applied to the dorsum by rubbing contact of the sponge upon dorsal surfaces.

After conditioning treatment of the dorsal surfaces through the application of a coating of the conditioning medium, the scraper head is inserted into the oral cavity and the dorsal surfaces are scraped by rubbing contact with an array of ribs which project from a lower face of the scraper head.

For complete removal of debris the opposite face of the scraper head is applied against the dorsum. The opposite face carries a peripheral array of teeth which engage the surface of the dorsum to remove debris.

From the foregoing compendium, it will be appreciated that it is an aspect of the present invention to provide a breath system appliance of the general character described which is not subject to the disadvantages of the antecedents of the invention aforementioned.

A feature of the present invention is to provide a breath system appliance of the general character described which is well suited to promote overall oral hygiene and to reduce the rate of plaque formation in the oral cavity.

A further aspect of the present invention is to provide a breath system appliance of the general character described which is simple to use.

Another further feature of the present invention is to provide a self-contained oral hygiene appliance of the general character described which is well suited to effectively dislodge debris from surfaces of the dorsum.

To provide a breath system appliance of the general character described which reduces the tendency of a user to gag is a still further aspect of the present invention.

Another consideration of the present invention is to provide a breath system appliance of the general character described which is portable and well suited for carrying about one's person for routine usage away from home.

Yet another feature of the present invention is to provide a breath system appliance of the general character described which is disposable and thus well suited for one time usage by hotel guests and the like as well as for promotional use.

It is a further aspect of the present invention to provide a breath system appliance of the general character described which is relatively low in cost and well suited for economic mass production fabrication.

Yet another consideration of the present invention is to provide a breath system appliance of the general character described wherein dorsal surfaces are coated with a conditioning medium for effective removal of food debris, bacteria and other risk factors associated with oral odor.

Yet another aspect of the present invention is to provide a breath system appliance of the general character described which is well suited to utilize any of a number of conditioning media or combinations thereof for efficacious treatment of oral malodor.

An additional feature of the present invention is to provide a breath system appliance of the general character described which dispenses a coating of liquid based conditioning medium for enhanced cleansing of dorsal surfaces.

A still further consideration of the present invention is to provide a breath system appliance of the general character described which is highly efficacious for both immediate and long term alleviation of oral malodor.

Other aspects, features and considerations of the present invention in part will be obvious and in part will be pointed out hereinafter.

With these ends in view, the invention finds embodiment and certain combinations of elements, arrangements of parts and series of steps by which the aforesaid aspects, features and considerations and certain other aspects, features and considerations are attained, or with reference to the accompanying drawings and the scope of which will be more particularly pointed out and indicated in the appended claims.

BRIEF DESCRIPTION OF THE DRAWINGS

In the accompanying drawings in which is shown one of the various possible exemplary embodiments of the invention.

DESCRIPTION OF THE PREFERRED EMBODIMENTS

Figure 1:
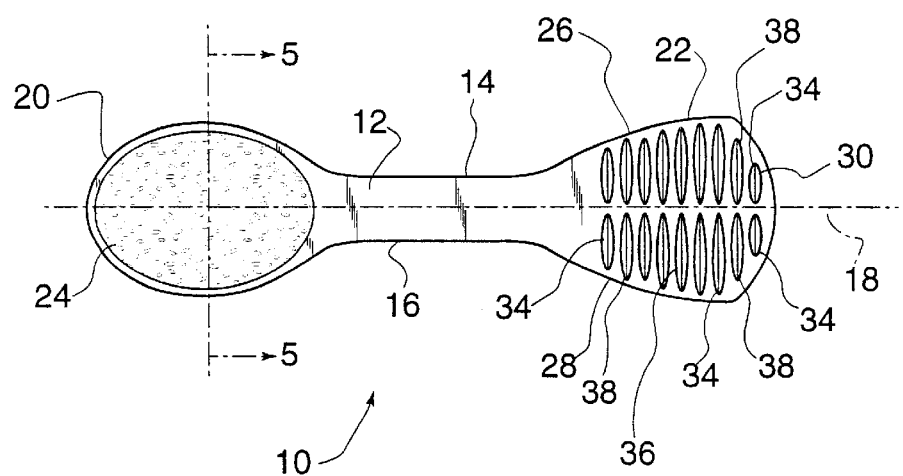
FIG. 1 is a bottom view of a breath system appliance constructed in accordance with and embodying the invention and showing an elongate planar body having at one end, an enlarged applicator head with a sponge adhered to its lower face and at its other end, an enlarged scraper head with an array of ribs projecting from its lower face.
Figure 2:
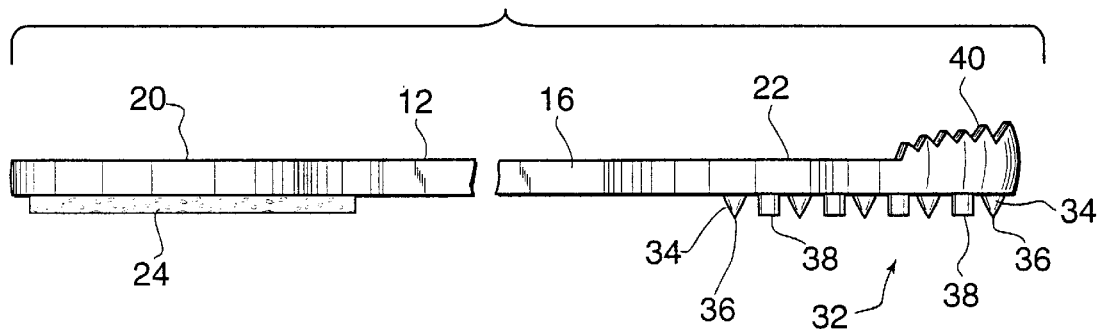
FIG. 2 is an enlarged scale side elevational view of the appliance and showing a plurality of teeth projecting from the upper face of the scraper head adjacent the periphery thereof.

Referring now in detail to the drawings, the reference numeral 10 denotes generally a breath system appliance constructed in accordance with and embodying the invention. The appliance comprises a generally flat relatively thin elongate body 12 having a pair of longitudinal side edges 14, 16 substantially parallel to a longitudinal axis, 18. Projecting transversely from the axis 18 at one end of the body 12 is an enlarged elliptical applicator head 20. At the opposite end of the body 12 is an enlarged paddle shaped scraper head 22 which also extends transversely from the longitudinal axis 18.

Adhered to the lower face of the applicator head 20 is an applicator sponge 24 which is elliptical in plan configuration, to conform to the peripheral contour of the applicator head 20. In accordance with the invention, the sponge 24 is saturated with a suitable dorsal conditioning medium carried in a liquid base.

The liquid based medium may include any of a number of agents or combinations thereof which have been established as being effective for oral cleansing and/or deodorizing including, but not limited to oxidizing agents, such as peroxides and stabilized chlorine dioxide. Antiseptic and antibacterial agents, astringent agents, flavoring agents and agents having anesthetizing attributes may also comprise constituents of the conditioning medium. Typical of such constituents are zinc chloride, thymol, eucalyptus oil and menthol.

The sponge 24 may be presaturated with the liquid based medium, in such instances, the breath system appliance 10 is packaged in a suitable foil or other liquid impervious packet 25. Optionally, the sponge 24 may be saturated prior to application as by the liquid based medium being dispensed on to the sponge 24 from a squeeze container, etc.

To apply the conditioning medium, the appliance 10 is grasped at the mid-portion of the body 12 and the applicator head 20 is inserted into the oral cavity with the sponge facing the user's tongue. The sponge 24 is pressed against and moved across the dorsal surfaces of the user's tongue to release a coating of conditioning medium over surfaces of the dorsum.

Alternately, the conditioning medium constituents may be in dry form carried within the sponge 24 for activation when ready to use. Activation may be effected either by immersion of the head 20 in water or through absorption of saliva by the sponge 24.

After the dorsum has been coated with the conditioning medium, the applicator head 20 is removed from the oral cavity and the scraper head 22, at the opposite end of the body 12, is inserted.

It should be noted that in plan configuration, the scraper head 22 differs from the applicator head 20. In lieu of having an elliptical plan configuration, the scraper head 22 has a generally paddle shaped configuration with a pair of diverging side edges 26, 28. A curved end surface 30 having a radius of curvature significantly larger than the radius of curvature of the end of the applicator head 20 is also found on the scraper head 22.

Figure 3:
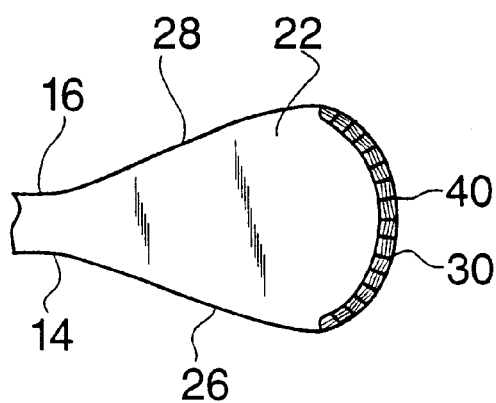
FIG. 3 is a fragmentary top plan view showing the peripheral teeth.
Figure 4:
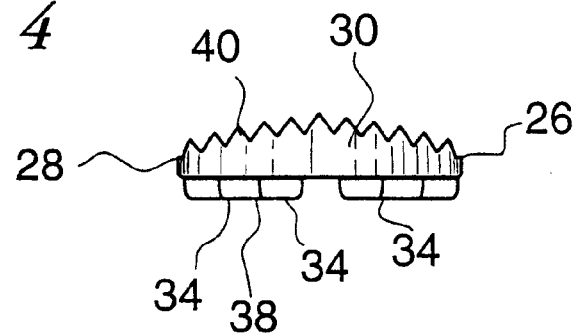
FIG. 4 is an enlarged scale right end view of the appliance showing the peripheral teeth projecting upwardly and the ribs projecting downwardly from opposite faces of the scraper head.
Figure 5:
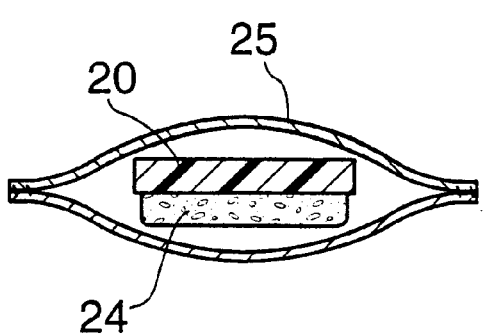
FIG. 5 is an enlarged sectional view through the appliance, the same being taken along line 5—5 of FIG. 1 and through a foil packet in which the appliance is sealed.

Symmetrically positioned along a lower face of the scraper head 22 is an array 32 of ribs 34, 38. As will be noted from an examination of FIG. 3, the array 32 is symmetric about the longitudinal axis 18. The array 32 includes rows of downwardly projecting transverse ribs 34, 38 with alternate ribs 34 having a relatively keen scraping edge 36 and with adjacent ribs 38 having terminal surfaces which are flat or blunted.

It should be noted that alternating rows of keen scraping edged and blunted edge ribs are but one of any number of rib configurations suitable for employment in the invention. All ribs could have blunted or keen edges and various combinations in between. Further, the array pattern, as well as the number of ribs may be varied without departing from the invention.

On the opposite or upper face of the scraper head 22 is a peripheral array of teeth 40.

In use, after the dorsum has been coated with the conditioning medium, the scraper head 22 is inserted into the oral cavity and either the array 32 of ribs 34, 38 on the lower face or the array of teeth 40 on the upper face are wiped against the dorsum in a back and forth, circular, oval or irregular scraping pattern.

The appliance 10 is then rotated about its axis 18 so that the opposite face of the scraper head 22 engages the dorsum and the wiping procedure is repeated.

It should be appreciated that the entire breath system appliance 10 can be suitably molded of one piece construction, with the exception of the sponge 24, from any of a number of known thermoplastics which are suited for use within the oral cavity including, but not limited to, polyethylene, polypropylene, acetals, polycarbonates, acrylonitrile-butanine-styrene, etc.

By way of example and not limitation, the appliance body 12 has length in the range of approximately 3 inches (75 mm.) to 4 inches (100 mm.) and preferably 3½ inches (90 mm.). The applicator and scraper heads may be dimensioned with a maximum transverse width in the order of ⅝ to ⅞ inches (16 to 23 mm.) and the thickness of the body 12 may range between 1 to 2 mm.

Figure 6:
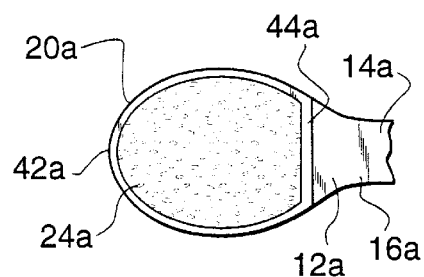
FIG. 6 is a fragmentary bottom view of an alternate embodiment wherein a sponge is retained by a peripheral wall.
Figure 7:
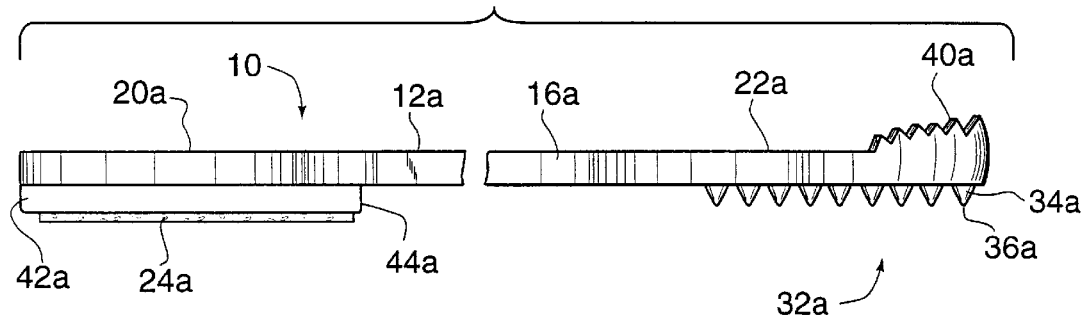
FIG. 7 is an enlarged scale side elevational view of the alternate embodiment showing the peripheral wall and an alternate array of ribs.

In FIGS. 6 and 7, there is illustrated an alternate embodiment of the invention wherein like numerals have been employed to denote like components of the previous embodiment, however, bearing the suffix "a". The alternate embodiment differs from the embodiment previously described in that an applicator sponge is circumscribed by a peripheral wall and further in that an array of ribs includes ribs with substantially uniform transverse cross section.

Referring now in detail to FIGS. 6 and 7, it will be seen that an appliance 10a includes a thin elongate body 12a having a pair of substantially parallel longitudinal side edges 14a, 16a. At one end of the body 12a, there is an elliptical applicator head 20a which carries a sponge 24a within a peripheral wall 42a. The wall 42a is substantially elliptical except for a truncation end wall 44a transverse to the longitudinal axis of the ellipse.

As seen from an examination of FIG. 7, the height of the peripheral wall 42a is slightly less than the thickness of the sponge 24a such that a surface of the sponge 42a is exposed for contact against the user's dorsal surfaces.

It should also be noted that the body 12a includes, at its opposite end, a scraper head 22a having a peripheral array of teeth 40a projecting from one face thereof and, projecting from the opposite face an array 32a of ribs 34a, each having a uniform transverse cross section with a longitudinal edge 36a. The edge 36a is slightly rounded, e.g. having a radius of 0.2 mm.

In all other aspects, the appliance 10a of the alternate embodiment is identical to that of the embodiment previously disclosed.

It should be understood that the conditioning medium serves manifold functions; one of its purposes is to provide a source of immediate breath freshening which benefit is derived from its flavoring constituents. It additionally serves to destroy odor causing bacteria and sulphites by conjunctive action of antiseptic and oxidizing agents. Further, the employment of astringent and/or anesthetizing agents is beneficial in reducing the gag reflex which may be encountered when the applicator and scraper heads approach and contact the pharyngeal surfaces of the dorsum. Gag reflex is also significantly reduced due to the overall low profile of the appliance.

A further significant function of the conditioning medium is to facilitate the dislodgement and removal of food and other debris which has accumulated on dorsal surfaces between the papillae. The conditioning medium thus enhances the efficacious results to be achieved through implementation of the scraper head.

Thus it will be seen that there is provided a breath system appliance which achieves the various aspects, features and considerations of the present invention and which is well-suited to meet the conditions of practical usage.

Since various possible embodiments might be made of the present invention and since various changes might be made in the exemplary embodiment shown herein without departing from the spirit of invention, it should be understood that all matter herein described or shown in the accompanying drawings should be interpreted as illustrative and not in a limiting sense.

What is claimed is:

1. An appliance for alleviation of oral malodor, the appliance comprising a generally planar thin elongate body, an applicator head at one end of the body and a dorsal scraper head at the other end of the body, the dorsal scraper head including a face, the face having an array of scraper elements, the applicator head including a sponge impregnated with a dorsal conditioning medium, whereby the conditioning medium is released from the sponge and applied as a coating to the dorsal surfaces of a user when the sponge engages a user's tongue and the scraper elements scrape dorsal surfaces of the user when the scraper head engages the user's tongue.

2. An appliance for alleviation of oral malodor as constructed in accordance with claim 1 wherein the scraper elements include relatively keen scraping edges, whereby effective dislodgement of debris carried on dorsal surfaces is achieved.

3. An appliance for alleviation of oral malodor as constructed in accordance with claim 1 wherein the scraper elements comprise rows of ribs, alternate ribs including keen edges and ribs adjacent the alternate ribs including blunt edges.

4. An appliance for alleviation of oral malodor as constructed in accordance with claim 1 wherein the scraper elements comprise ribs and the dorsal scraper head includes a further face, the further face having a plurality of teeth projecting therefrom in a direction opposite that of the ribs, the teeth being positioned along a peripheral edge of the dorsal scraper head.

5. An appliance for alleviation of oral malodor as constructed in accordance with claim 4 wherein the further face of the dorsal scraper head is smooth, except along the peripheral edge.

6. An appliance for alleviation of oral malodor as constructed in accordance with claim 1 wherein the conditioning medium comprises anesthetizing constituents carried in a liquid base.

7. An appliance for alleviation of oral malodor as constructed in accordance with claim 6 wherein the conditioning medium includes a constituent selected from the group consisting of zinc chloride, thymol, eucalyptus oil, menthol, peroxides and chlorine dioxide.

8. An appliance for alleviation of oral malodor as constructed in accordance with claim 1 wherein the conditioning medium is carried in the sponge in dry form, the conditioning medium being activated by a liquid.

9. An appliance for alleviation of oral malodor as constructed in accordance with claim 8 wherein the liquid comprises saliva.

10. An appliance for alleviation of oral malodor as constructed in accordance with claim 1 wherein the scraper elements comprise teeth.

11. An appliance for alleviation of oral malodor as constructed in accordance with claim 1 wherein the applicator head includes a face, the sponge being positioned against the face, the sponge having a thickness and a periphery, the applicator head including a wall surrounding the sponge periphery, the wall having a height less than the thickness of the sponge.

12. An appliance for alleviation of oral malodor and a liquid impervious packet, the appliance comprising a thin generally flat body having an applicator at one end thereof and a dorsal scraper at the other end thereof, a supply of liquid based conditioning medium being carried at the applicator, the conditioning medium including a constituent selected from the group consisting of zinc chloride, thymol, eucalyptus oil, menthol, peroxides and chlorine dioxide, the appliance being sealed within the packet.

13. An appliance for alleviation of oral malodor as constructed in accordance with claim 12 wherein the scraper includes an array of ribs whereby dorsal surfaces of a user may be cleansed when the scraper engages the user's tongue.

14. An appliance for alleviation of oral malodor as constructed in accordance with claim 12 wherein the scraper further includes an array of teeth whereby dorsal surfaces of the user may be cleansed when the scraper engages a user's tongue.

15. An appliance for alleviation of oral malodor as constructed in accordance with claim 12 wherein the scraper includes two generally planar faces, an array of ribs projecting from one face and an array of teeth projecting from the other face.

16. A treatment for alleviation of oral malodor in a person, the treatment comprising:
 a) coating dorsal surfaces of the person's tongue with a conditioning medium having a constituent selected from the group consisting of zinc chloride, thymol, eucalyptus oil, menthol, peroxides and chlorine dioxide, and
 b) thereafter scraping the coated dorsal surfaces.

17. A treatment for alleviation of oral malodor in accordance with claim 16 wherein the step of scraping the coated dorsal surfaces includes scraping with a plurality of ribs projecting from a flat surface.

18. A treatment for alleviation of oral malodor in accordance with claim 17 wherein the step of scraping includes scraping the coated dorsal surfaces with a plurality of teeth projecting from a flat surface.

19. A treatment for alleviation of oral malodor in accordance with claim 17 wherein the step of coating dorsal surfaces with a conditioning medium includes applying a sponge carrying the conditioning medium against the dorsal surfaces.

* * * * *